US005718709A

United States Patent [19]
Considine et al.

[11] Patent Number: 5,718,709
[45] Date of Patent: *Feb. 17, 1998

[54] APPARATUS FOR REMOVING TUMOURS FROM HOLLOW ORGANS OF THE BODY

[76] Inventors: John Considine, 8 Reddings Rd., Moseley, Birmingham, England, B12 8LN; Colin John Bunce, 49 Elderpark Gardens, Gover, Glasgow, Scotland, G51 3NX

[*] Notice: The portion of the term of this patent subsequent to Jan. 14, 2014, has been disclaimed.

[21] Appl. No.: 471,735

[22] Filed: Jun. 6, 1995

Related U.S. Application Data

[63] Continuation of Ser. No. 181,886, Jan. 14, 1994, Pat. No. 5,441,503, which is a continuation of Ser. No. 671,787, May 20, 1991, abandoned.

[30] Foreign Application Priority Data

Sep. 24, 1988 [GB] United Kingdom .................. 8822492

[51] Int. Cl.⁶ .................................................. A61B 17/36
[52] U.S. Cl. .................................. 606/115; 606/46
[58] Field of Search ........................ 600/101, 104; 604/20, 22, 190, 164, 264, 270, 272, 902; 606/1, 27–29, 34–52, 106–108, 127–129, 167, 170, 115, 110–114

[56] References Cited

U.S. PATENT DOCUMENTS

| | | | |
|---|---|---|---|
| 1,952,617 | 3/1934 | Wappler | 606/48 |
| 2,038,393 | 4/1936 | Wappler . | |
| 2,102,270 | 12/1937 | Hyams . | |
| 2,888,017 | 5/1959 | Wallace | 606/46 |
| 2,888,928 | 6/1959 | Seiger . | |

(List continued on next page.)

FOREIGN PATENT DOCUMENTS

| | | | |
|---|---|---|---|
| 0189329 | 7/1986 | European Pat. Off. . | |
| 2594322 | 8/1987 | France . | |
| 1947123 | 3/1970 | Germany . | |
| 2324415 | 10/1974 | Germany . | |
| 2449559 | 4/1976 | Germany | 606/46 |
| 2521719 | 11/1976 | Germany | 606/46 |
| 2628555 | 12/1977 | Germany | 606/46 |
| 2747031 | 5/1979 | Germany | 606/128 |
| 3013784 | 10/1980 | Germany | 606/46 |
| 3313325 | 10/1984 | Germany . | |
| 3543173 | 6/1986 | Germany | 606/46 |
| 3543594 | 7/1986 | Germany . | |
| 0221209 | 10/1968 | U.S.S.R. | 606/128 |
| 502607 | 4/1939 | United Kingdom . | |
| 2053691 | 2/1981 | United Kingdom | 606/46 |
| 2144638 | 3/1985 | United Kingdom | 606/128 |
| WO82/03545 | 10/1982 | WIPO . | |
| WO8403829 | 10/1984 | WIPO . | |

OTHER PUBLICATIONS

Journal of the Royal Society of Medicine, vol. 74, Jul. 1981, "Adjuvant Chemotherapy in Bladder Cancer", pp. 547–550.

Primary Examiner—Glenn K. Dawson
Attorney, Agent, or Firm—Peter J. Manus, Esq.

[57] ABSTRACT

An endoscope for use in the removal of tumors from hollow body organs such as the bladder. The endoscope consists of a sheath (49) through which extends a telescope (40) and a suction diathermy tube (2, 31, 60) the non-operation end (3, 33) of which communicates with a suction device. Provision (51, 52) is made for an irrigation fluid to be passed through the endoscope. The diathermy tube (2, 31, 60) has an electrode tip (7, 8) which may be formed from electrically conducting resistance wire connected (5, 39, 63) to a diathermy machine. The electrode tip is found adjacent an aperture (4, 9, 41) at the operative of the tube whereby tissue can be immediately removed by suction after severance by the electrode tip. The degree of suction applied to the tube (2, 31, 61) is controlled by a finger hole (38a, 55, 66) located at or near the end (3, 33) of the tube (2, 31, 61). Alternatively the tube (31) may be formed of a metal tube (34) coated with an insulating plastics material (35) and having a cutting or coagulating tip (34a), provision (37, 38, 43, 45, 53, 54) being made for reciprocating the tube up and down the endoscope.

14 Claims, 5 Drawing Sheets

U.S. PATENT DOCUMENTS

| | | |
|---|---|---|
| 3,661,144 | 5/1972 | Jensen et al. . |
| 3,828,780 | 8/1974 | Morrison, Jr. . |
| 3,835,842 | 9/1974 | Iglesias . |
| 3,850,175 | 11/1974 | Iglesias . |
| 3,902,494 | 9/1975 | Haberlen et al. . |
| 3,974,833 | 8/1976 | Durden, III . |
| 3,990,456 | 11/1976 | Iglesias . |
| 4,030,502 | 6/1977 | Iglesias . |
| 4,060,086 | 11/1977 | Storz . |
| 4,311,143 | 1/1982 | Komiya . |
| 4,430,996 | 2/1984 | Bonnet ........... 606/46 |
| 4,474,174 | 10/1984 | Petruzzi ........... 606/46 |
| 4,643,197 | 2/1987 | Greene et al. . |
| 4,657,018 | 4/1987 | Hakky . |
| 4,682,596 | 7/1987 | Bales et al. . |
| 4,724,836 | 2/1988 | Okada . |
| 4,726,370 | 2/1988 | Karasawa et al. ........... 606/46 |
| 4,756,309 | 7/1988 | Sachse et al. ........... 606/170 |
| 4,998,527 | 3/1991 | Meyer . |

APPARATUS FOR REMOVING TUMOURS FROM HOLLOW ORGANS OF THE BODY

This is a continuation of application Ser. No. 08/181,886 filed on Jan. 14, 1994, now U.S. Pat. No. 5,441,503 which is a continuation of Ser. No. 07/671,787 filed on May 20, 1991, now abandoned.

The present invention relates to an apparatus for the removal of tumours from hollow body organs accessible to an endoscope, and in particular the removal of tumours from the bladder.

The removal of tumours from hollow organs of the body by surgery frequently results in the release of viable free tumour cells which may gain attachment to the mucosa thereby resulting in the reoccurrence of tumours.

Removal of tumours from the bladder is generally achieved either by an open operation (supra-pubic diathermy excision) or by transurethral resection (TURO). It has been suggested by Smith [J.R.S.H. 74 547 to 550 (1981)], among others, that the implantation of free tumour cells may be enhanced by instrumental damage to the mucosa during the evacuation of tumour fragments by TUR. To overcome this problem intravesical installations of cytotoxic drugs have been examined [Zinck et al Journal of Urology 134 1110–1114 (1985)]. In open surgery it is usual for friable superficial portions of the tumour to be removed via a suction tube inserted through the first opening made in the bladder wall before the normal tissues are exposed to contamination. The application of this technique to TUR is expected to reduce the rate of recurrence of tumours resulting from TUR resection.

An apparatus for use in the removal of tumours from hollow body organs accessible to an endoscope comprising, in combination, an endoscope (4) having a closed end (42) through which the telescope (46) passes, an open operative end (41) and a diathermy suction tube (2, 31, 61) extending through the closed end (42) of the said endoscope to the open end (41) and including an operative end (4, 9, 32) having an exposed electrode tip (7, 8, 10, 34a, 62) portion adjacent to an opening in or at the said operative end of the tube, the said electrode (7, 8, 10, 34a, 62) being connected (5, 39, 56, 63) to a source of electrical power and the other end of the diathermy suction tube (2, 31, 62) connected to a vacuum source (50, 65), characterised in that means (51, 52) are provided for the introduction of an irrigation fluid into the endoscope (40) adjacent the closed end (42) thereof; said diathermy tube (2, 31, 61) being retractable along the endoscope whereby the operative electrode tip (7, 8, 10, 34a, 62) may be withdrawn within the endoscope 40 during insertion into the body organ and thereafter advanced into the tumour whilst maintaining an exit for the severed tumour and irrigating fluid.

The said opening in the tubing may be formed at the end of the tube i.e., the tube may be open-ended, or in a sidewall adjacent to the end thereof. Additional small openings in the tube sidewall may also be provided if required.

In one form the diathermy tube is formed from flexible translucent plastics material and the said diathermy electrode tip is formed of electrically conductive resistance wire connected to the source of electrical power by at least one electrically conductive wire located in the wall of the said tube.

The diathermy electrode wires are preferably embedded in the wall of the tubing but may, also, for example be secured along an outside wall.

It is preferred that the electrode is connected to two wires passing along diametrically opposed portions of the tubing wall.

The exposed tip of the electrode may be formed in any convenient shape, for example it may be a wire having a circular or semi-circular shape preferably of the same diameter as the internal diameter of the opening in the tubing. The wire may be in contact with the wall of the opening or spaced therefrom and may be parallel or at an angle to the face of the opening.

In one form the diathermy tube is formed from an electrically conductive metallic tube coated with an insulating material, the operative tip portion of tube being left bare to provide a diathermy electrode, the said tip portion extending beyond the open end of the cystoscope, the tube being connected to a source of electrical power by electrically conductive wires making contact with the opposite end thereof.

In another form the suction tube is formed from spirally wound wires coated with polytetrafluoroethylene (PTFE), the electrode tip being formed at an uncoated end of the tube, e.g. at the junction of the wires. A single double wound wire may, of course, be used in place of two wires.

A specimen collection vessel may be connected between the end of the tubing and the suction means. The specimen vessel may be in the form of an elongated cylindrical body separable into two portions, the upper portion including an inlet pipe for connection with the said tubing and means for adjusting the suction applied to the tubing and the lower portion including an outlet pipe for connection with the suction means and containing a replaceable filter in which the specimen is collected. The suction adjustment means may be a finger hole formed in the side of the said upper portion or at the end of a pipe communicating therewith.

In one embodiment of the invention a double channel endoscope is employed in which the two channels extending along only a short length of the endoscope before merging into a single channel, the flexible translucent suction tube passes through one channel and the electrode wires, which are not embedded in the tube, through the second channel, where the two channels merge into a single channel the electrode wires then run parallel and adjacent the tubing and arm secured to the tubing near the open end in order to maintain the spatial relationship between the electrode tip and tube opening. In another embodiment of the present invention the diathermy tube is a rigid instrument that may be employed in co-operation with advancing mechanism of a urethrotome or the retracting mechanism of a resectoscope. In this apparatus, a rigid insulated metal combined suction and diathermy tube is used, the operative exposed electrode of the mechanism being the distal circumference of the tube or, alternatively, a lateral window formed in the tube wall.

The invention will now be more fully described with reference to the accompanying drawings in which.

Figure 3:
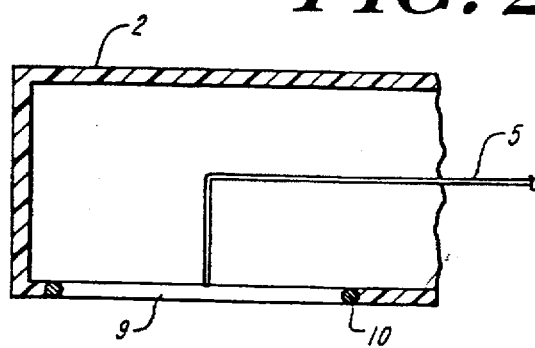
Figure 4:
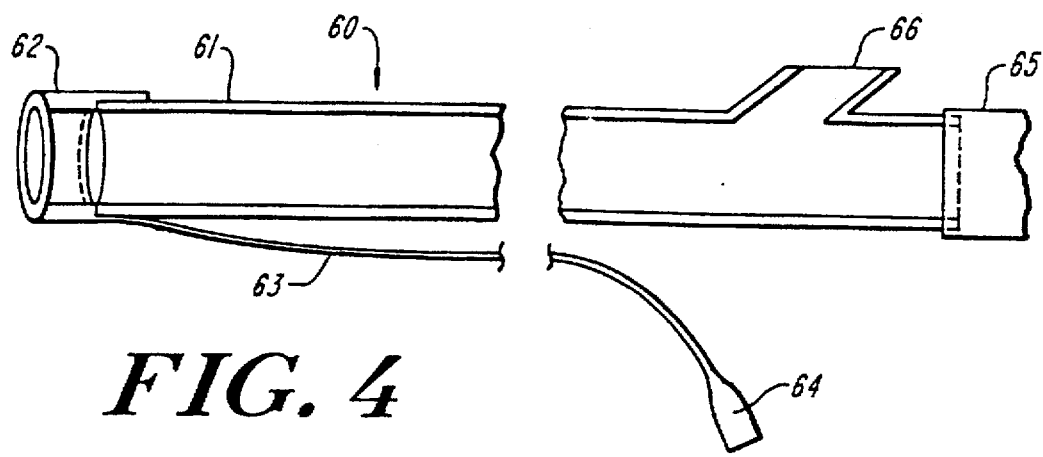
Figure 5:
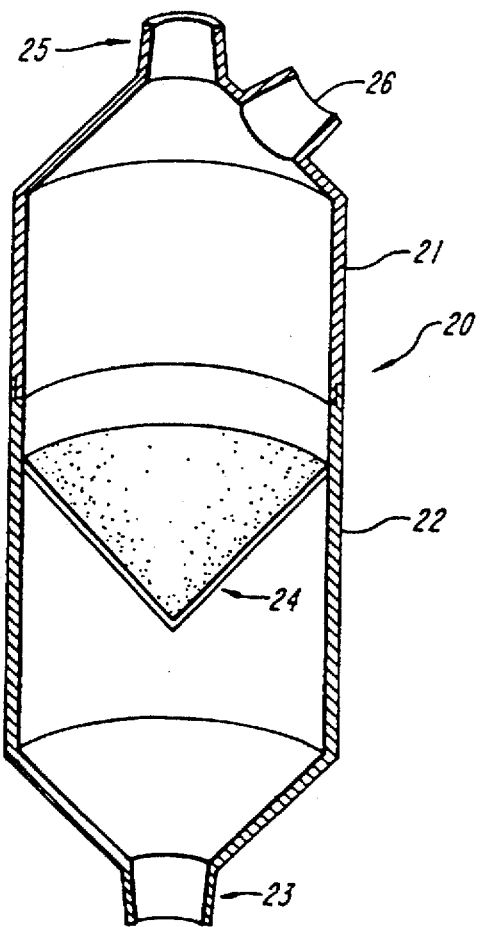
Figure 6:
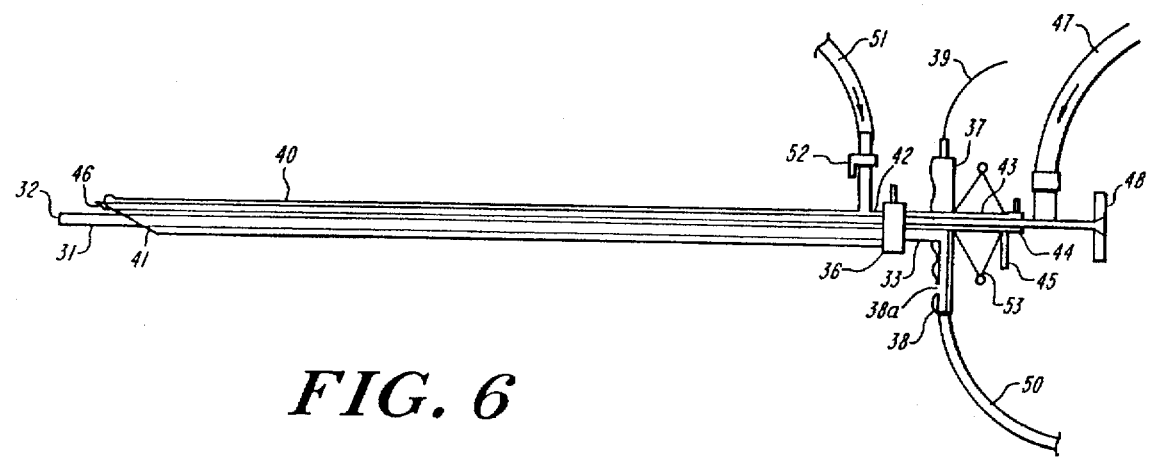
Figure 7:
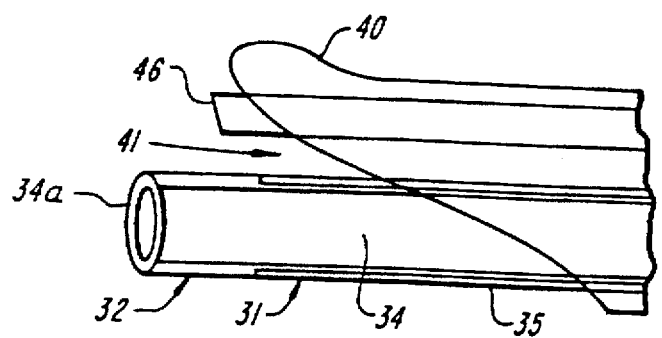
Figure 8:
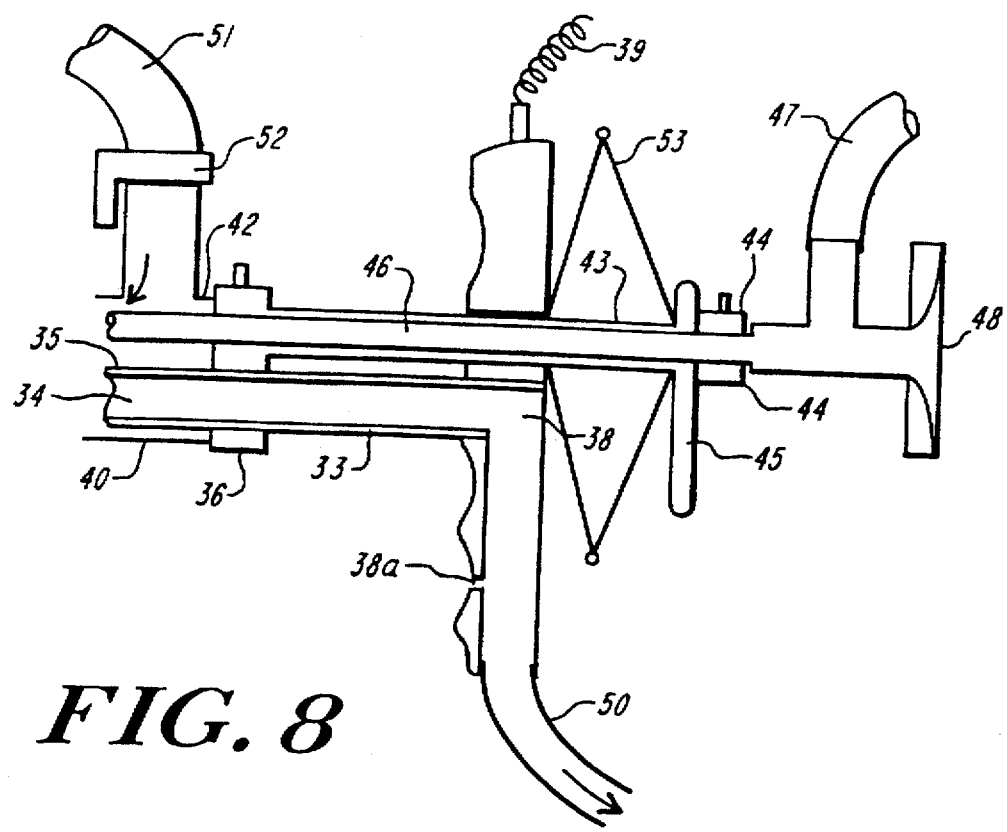
Figure 9:
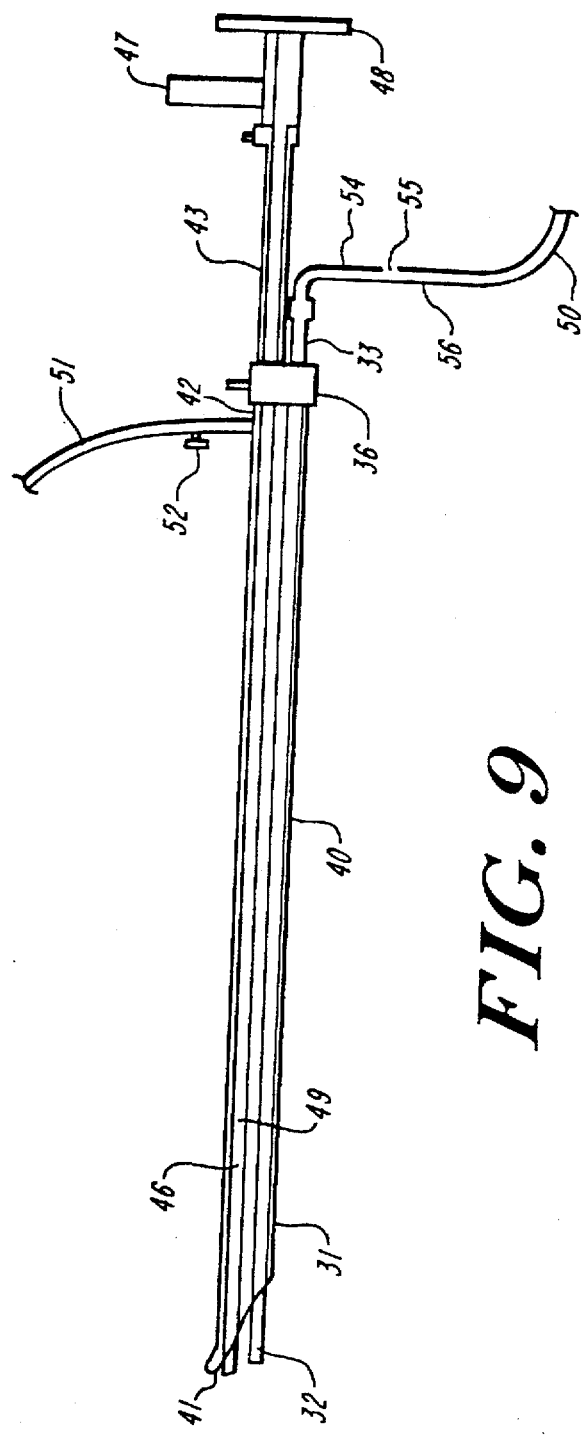

FIG. 3 is a side view of a third form of diathermy tube for use with the present invention, FIG. 4 is a side view of a fourth form of diathermy tube for use with the present invention, FIG. 5 is a diagramatic section through a specimen vessel for use with the present invention, FIG. 6 is a diagramatic illustration of one embodiment of the present invention, FIG. 7 is an illustration of the operative end of the device of FIG. 6, FIG. 8 is an illustration of the other end of the device of FIG. 6, and FIG. 9 is a diagramatic illustration of another embodiment of the present invention.

Figure 1:
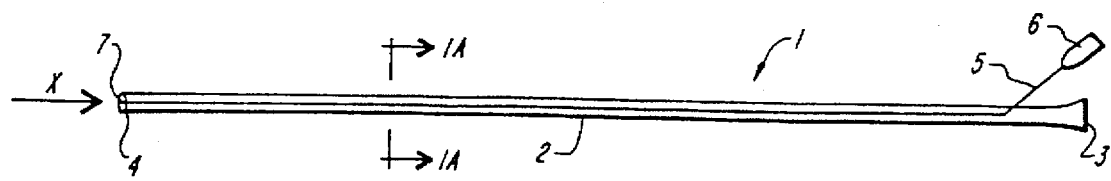
FIG. 1 is a side view of a diathermy tube for use in the invention.
Figure 1A:
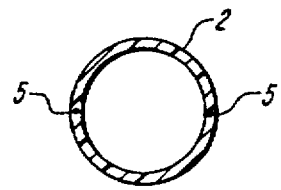
FIG. 1a is a cross section through A—A of FIG. 1.
Figure 1B:
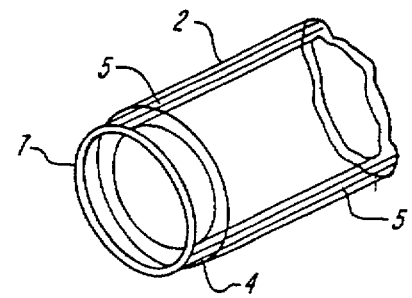
FIG. 1b is a perspective view of a fragment of the apparatus FIG. 1 in the direction X.

The diathermy tube of FIG. 1 comprises a translucent flexible plastics tube 2 having an end 3 adapted for connection to a suitable suction apparatus, and an open end 4.

Figure 2B:
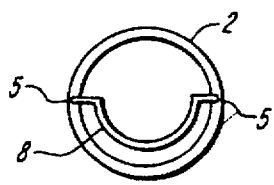
FIG. 2b is an end view of the embodiment FIG. 2 in the direction Y.
Figure 2:
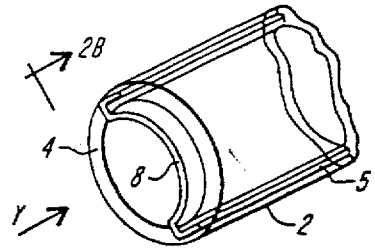
FIG. 2 is a perspective view of a fragment of an alternative form of diathermy tube for use with the present invention.

Twin electrode wires 5, have ends 6 connected to a diathermy apparatus and extend lengthwise of, and are embedded in, the walls of the tube at opposite ends of a diameter thereof. An exposed tip of the electrode 7 extends beyond the open end of the tube and is in the form of a circular wire ring spaced from end 4 of tube 2. In the diathermy tube of FIG. 2 the exposed end 8 of the electrode wires 5 is in the form of a semi-circular wire ring adjacent to end 4 of tube 2.

Suction through the diathermy tube is controlled by an aperture, which may be partially or fully closed by an operative'finger, formed at the end of the tube adjacent the connection to the suction source or at a point in the means connecting the tube to the said source, e.g. in a specimen collection vessel.

In the diathermy tube of FIG. 3 the opening 9 in tube 2 is formed in the side wall thereof adjacent to a closed end and the exposed tip of electrode 10 is in a form of a circular wire located within the circumference of the opening.

In FIG. 4 a diathermy tube, generally indicated at 60 consists of a hollow plastics suction tube 61 having a removable diathermy electric tip 62 connected to a source of electrical power by leads 63 and connector 64. The non-operative end of the tube is connected to a suction device via tube 65 and includes a finger hole 66 to control the degree of suction applied to tube 61. The connector 64 and lead 63 are passed retrogradely through the endoscope from the operative end so that the connector 64 can be connected to a source of electrical power at the other end. The suction tube 61 is then passed down through the endoscope and the electrode tip inserted over it's end, the tip being a press fit over the end of the tube 61.

A suitable specimen collecting vessel is illustrated in FIG. 5. The vessel, generally indicated at 20, comprises two portions 21 and 22 in screw-threaded engagement. Portion 22 contains a pipe 23 for attachment to a suitable suction means such as a vacuum pump and further includes a replaceable specimen filter 24 on which tumour portions may be collected. Portion 21 includes a pipe 25 for attachment to the end 3 of tube 2 and further includes a finger hole at 26 enabling the vacuum applied through end 23 to be manually adjusted.

A complete apparatus of invention is illustrated in FIGS. 6, 7 and 8.

A hollow diathermy suction tube 31 having end portions 32 and 33 extends through an endoscope sheath 40 having an open operative end 41 and a closed end 42. Tube 31 consists of an inner chemically inert electrically conducting tube 34, such as stainless steel, covered with an insulating sheath 35 formed of insulating plastics material, such as PTFE, except for end portion 32 which is left bare and which provides the cutting or coagulating electrode tip 34a. End 33 of tube 31 is slidably supported in a bush member 36, which acts to close end 42 of endoscope sheath 40, in a fluid tight manner. End 33 is releasably secured to the hollow arm 38 of a hand piece 37 to make electrical contact with lead 39 of a diathermy unit (not shown). Hand piece 37 is, in turn, slidably supported on a tubular member 43 secured through bush 36 and extending rearwardly therefrom. Hollow arm 38 of hand piece 37 is attached to a tube 50 communicating with a suction device via an optional specimen collection vessel (not shown) and contains an aperture 38a open to the atmosphere and positioned to permit it to be fully or partially closed by a finger of a user. A thumb plate 45 is provided at the end 44 of tubular support 43. A telescope 46 extends from the open end 42 of the endoscope tube 40 through bush 36 and tubular member 43 and is provided with a light source 47 and an eye piece 48. A washer 49 is located at the end of the telescope 46 adjacent the end of tubular member 43 to make fluid tight contact therewith to prevent fluid seeping through and out of member 43. An irrigation fluid inlet 51 and tap 52 communicates with end 42 of endoscope 40 forward of bush 36. A spring member 53 is positioned between thumb plate 45 and hand piece 37 to normally urge the hand piece and therefore the diathermy tube 31 fully forward.

When in use the diathermy tube 31 is initially retracted within the endoscope tube 40 by the user applying pressure between the thumb plate 45 and the hand piece 37 and compressing spring 53. The endoscope 40 is then directed into the body organ from which a tumour, for example, is to be removed. The degree of suction applied at the operative end of the diathermy tube is controlled by finger pressure on aperture 38a. The position of the tumour is observed through the telescope 46 and the diathermy tube allowed to move forward under the influence of spring 53. Power from the diathermy unit is switched on and a portion of the tumour cut away by the heated end 32 of the diathermy tube and the severed tissue immediately removed by suction through the open end of the diathermy tube and pipe 50 to a waste collection means. Irrigation fluid is caused to pass into the organ via the tube 51 and endoscope 40 and is sucked away together with blood and severed tissue through the open end of the diathermy tube and through pipe 50 to a waste collection means.

In a simplified form of the apparatus described with reference to FIGS. 6, 7 and 8 and illustrated in FIG. 9, in which like parts have like references, handle 37 is omitted and replaced by end 33 of tube 31 which is bent through 90° to provide an arm 54. A finger aperture 55 is provided in arm 54 to control the degree of suction through the tube. Connection to a diathermy device (or other source of electrical power) is achieved via leads 56 secured via a suitable plug means to arm 54. Movement of the diathermy tube 31 up and down the cystoscope is controlled by the user holding the arm 54.

We claim:

1. An apparatus for use in the removal of tumours from the urinary tract of a body comprising, in combination, an endoscope having a first end through which a telescope passes, which end is sealed against the egress of fluid, a second open operative end, a diathermy suction tube having a wall extending through said first end of said endoscope to the open end, to provide an uninterrupted channel therethrough, and means for the continuous introduction of an irrigation fluid into said endoscope adjacent said first end thereof for passage therethrough around said diathermy suction tube with an annular clearance and out of the second open operative end, said diathermy suction tube including a first operative tube end having an exposed electrode tip portion adjacent to an opening at the said operative end of said tube, said electrode being connected to a source of electrical power, a second end, remote from said operative tube end and connected to a vacuum source, said suction diathermy tube being retractable along the endoscope whereby the operative tube end thereof including the exposed portion may be withdrawn within the endoscope during insertion of the said endoscope into the urinary tract and thereafter advanced into the tumour whilst maintaining an exit for the severed tumour and irrigating fluid, the relative locations of the electrode tip and the said opening in the diathermy suction tube being such that the severed tumor, irrigating fluid and body fluids are immediately withdrawn through the said tube thereby reducing the likelihood of tumour cells gaining attachment to the urinary tract mucosa.

2. An apparatus according to claim 1 wherein means are provided adjacent the second end of the diathermy suction tube to control the degree of suction applied to the said diathermy suction tube.

3. An apparatus to claim 1 or 2 wherein the diathermy suction tube is formed from flexible translucent plastics material and the said electrode tip is formed of electrically conductive resistance wire connected to the source of electrical power by at least one electrically conductive wire located along the wall of the said diathermy suction tube.

4. An apparatus according to claim 3 wherein said at least one electrical conductive wire is two wires and wherein the electrode tip is formed at the end of said two.

5. An apparatus according to claim 4 wherein the wires are embedded in the wall of the diathermy suction tube.

6. An apparatus according to claim 3 wherein the electrode tip is releasably attached to the second operative end of the diathermy suction tube.

7. An apparatus according to claim 3 wherein said at least one electrically conductive wire is a pair of spirally wound electrically conductive wires joined at one end to form said electrode tip and coated with an insulating plastics material from a point adjacent, but not including, said electrode tip.

8. An apparatus according to claim 1 or 2 wherein the diathermy suction tube is formed from an electrically conductive metallic tube coated with an insulating material, the operative end of said diathermy suction tube being left bare to provide a diathermy electrode, the said operative end of said diathermy suction tube extending beyond the open end of the endoscope, the diathermy suction tube being connected to the source of electrical power by electrically conductive wires making contact with the second end of said suction diathermy tube.

9. An apparatus according to claim 8 wherein the diathermy suction tube extends slidably through the closed end of the endoscope and the second end of said diathermy suction tube includes a handle supported on means extending coaxially of the endoscope; a portion of said handle is hollow and is in fluid communication with the diathermy suction tube and with the said vacuum source.

10. An apparatus according to claim 9 further comprising means to control the degree of suction in said diathermy suction tube including an aperture (38a) formed in said handle (37) normally open to the atmosphere and communicating with the hollow portion (38) thereof.

11. An apparatus according to claim 8 further comprising tubular support means extending from the endoscope through which the telescope extends.

12. An apparatus according to claim 8 of said diathermy suction tube extending outwardly of the endoscope and being bent through an angle to provide an arm whereby the diathermy suction tube may be moved along the endoscope.

13. An apparatus according to claims 1 or 2 wherein a specimen collecting vessel is in fluid communication with and between the diathermy suction tube and the vacuum source.

14. An apparatus according to claim 13 wherein the specimen collecting vessel includes a replaceable filter for the collection of tissue samples.

* * * * *